(12) United States Patent
Gil et al.

(10) Patent No.: US 8,221,423 B2
(45) Date of Patent: Jul. 17, 2012

(54) OSTEOCHONDRAL PLUG GRAFT HARVESTING INSTRUMENT AND KIT

(75) Inventors: Carlos E Gil, Collierville, TN (US); Jeetendra S Bharadwaj, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1048 days.

(21) Appl. No.: 11/390,217

(22) Filed: Mar. 28, 2006

(65) Prior Publication Data
US 2007/0270711 A1    Nov. 22, 2007

(51) Int. Cl.
*A61B 17/32* (2006.01)
(52) U.S. Cl. ............... 606/80; 606/87; 606/96; 606/180
(58) Field of Classification Search .............. 606/79, 606/81–89, 86 R, 96, 104, 198, 323, 180; 408/204, 207, 230
See application file for complete search history.

(56) References Cited

U.S. PATENT DOCUMENTS

| | | | | |
|---|---|---|---|---|
| 2,401,548 | A | * | 6/1946 | Chapman ...................... 606/172 |
| 2,794,469 | A | * | 6/1957 | Shortell ........................ 408/206 |
| 4,573,838 | A | * | 3/1986 | Omi et al. .................... 408/204 |
| 4,649,918 | A | * | 3/1987 | Pegg et al. .................... 606/79 |
| 4,696,308 | A | * | 9/1987 | Meller et al. ................. 600/567 |
| 4,820,156 | A | * | 4/1989 | Ross ............................. 433/165 |
| 4,821,716 | A | * | 4/1989 | Ghajar et al. ................. 606/172 |
| 5,054,971 | A | * | 10/1991 | Kieninger et al. ........... 408/205 |
| 5,069,584 | A | * | 12/1991 | Obermeier et al. .......... 408/145 |
| 5,207,681 | A | * | 5/1993 | Ghadjar et al. ................ 606/96 |
| 5,366,374 | A | * | 11/1994 | Vlassis ......................... 433/165 |
| 5,401,125 | A | * | 3/1995 | Sevack et al. .............. 408/203.5 |
| 5,632,745 | A | | 5/1997 | Schwartz |
| 5,632,747 | A | * | 5/1997 | Scarborough et al. .......... 606/79 |
| 5,772,664 | A | * | 6/1998 | DeSatnick et al. .............. 606/80 |
| 5,817,098 | A | * | 10/1998 | Albrektsson et al. ........... 606/96 |
| 5,833,628 | A | * | 11/1998 | Yuan et al. .................... 600/567 |
| 5,895,389 | A | * | 4/1999 | Schenk et al. .................. 606/96 |
| 5,919,196 | A | * | 7/1999 | Bobic et al. ................. 606/86 R |
| 5,921,987 | A | * | 7/1999 | Stone .............................. 606/80 |
| 6,017,348 | A | * | 1/2000 | Hart et al. ....................... 606/79 |
| 6,146,385 | A | * | 11/2000 | Torrie et al. .................... 606/96 |
| 6,306,142 | B1 | * | 10/2001 | Johanson et al. ............... 606/79 |
| 6,358,253 | B1 | | 3/2002 | Torrie |
| 6,375,658 | B1 | * | 4/2002 | Hangody et al. ............... 606/80 |
| 6,423,073 | B2 | | 7/2002 | Bowman |
| 6,520,964 | B2 | | 2/2003 | Tallarida |
| 6,530,928 | B1 | | 3/2003 | Frei |
| 6,610,067 | B2 | | 8/2003 | Tallarida |
| 6,827,722 | B1 | * | 12/2004 | Schoenefeld ................. 606/104 |
| 6,869,282 | B2 | | 3/2005 | Carmichael |
| 6,884,245 | B2 | * | 4/2005 | Spranza, III .................... 606/79 |

(Continued)

FOREIGN PATENT DOCUMENTS
EP    1 481 651    1/2004

*Primary Examiner* — Thomas C. Barrett
*Assistant Examiner* — Larry E Waggle, Jr.

(57) ABSTRACT

An instrument for harvesting an osteochondral plug graft in an implantable configuration, comprises a support pod comprising an elongated tubular member distally terminating in at least three splayed legs; a drill bit encompassed within a longitudinal axis of the tubular member; and a guide wire encompassed within a longitudinal axis of passageway of the drill bit and terminating at a threaded distal end for removably fixing a distal end of the instrument in a position oriented normal to an osteochondral surface for harvesting an osteochondral plug graft in an implantable normal configuration.

13 Claims, 4 Drawing Sheets

U.S. PATENT DOCUMENTS

| | | | |
|---|---|---|---|
| 2001/0018583 A1* | 8/2001 | Bays | 604/516 |
| 2002/0198532 A1* | 12/2002 | Michelson | 606/90 |
| 2004/0034437 A1* | 2/2004 | Schmieding | 623/908 |
| 2004/0243132 A1 | 12/2004 | Whittaker | |
| 2005/0137600 A1* | 6/2005 | Jacobs et al. | 606/79 |
| 2006/0173476 A1* | 8/2006 | Bradica et al. | 606/179 |

* cited by examiner

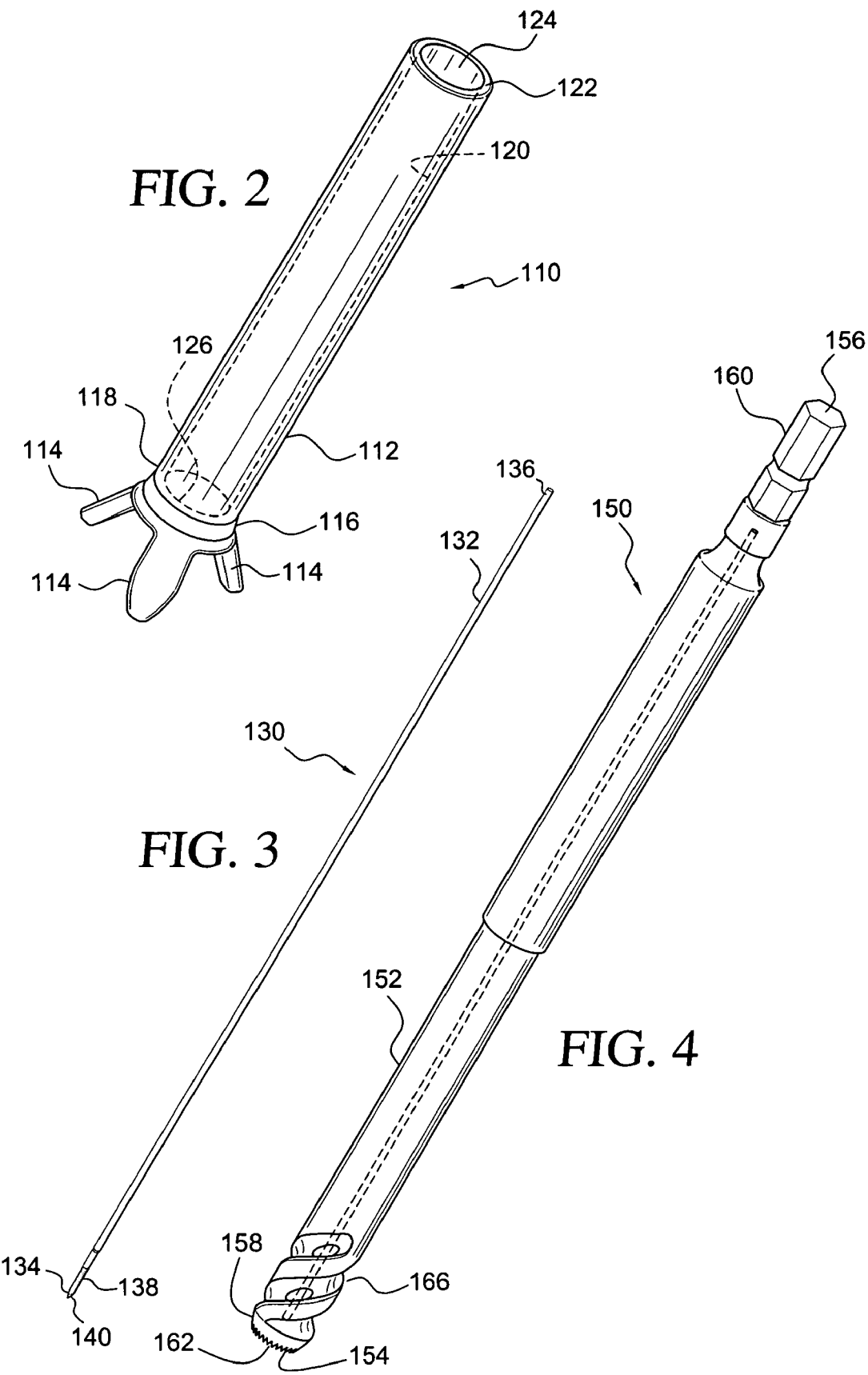

OSTEOCHONDRAL PLUG GRAFT HARVESTING INSTRUMENT AND KIT

BACKGROUND OF THE INVENTION

The invention relates to an osteochondral plug graft instrument, kit and method. More particularly, the invention relates to an instrument to harvest an osteochondral plug graft for implant in osteochondral tissue in need of repair. Also, the invention relates to a kit including the instrument and to a method to use the instrument.

Human joint surfaces are covered by articular cartilage that provides a resilient, durable surface with low friction. Cartilage is an avascular tissue that has a small number of chondrocytes encapsulated within an extensive extracellular matrix. The cartilage acts to distribute mechanical forces and to protect subchondral bone. The knee is a particular instance of a cartilage surfaced (the condyle) bone area. The knee comprises three bones—the femur, tibia, and patella that are held in place by various ligaments. Corresponding chondral areas of the femur and the tibia form a hinge joint and the patella protects the joint. Portions of the chondral areas as well as the underside of the patella are covered with an articular cartilage that allows the femur and the tibia to smoothly glide against each other without causing damage.

Damage to the articular cartilage, subchondral bone or both can result from traumatic injury or a disease state. For example, articular cartilage in the knee can tear due to traumatic injury as with athletes and degenerative processes as with older patients. The knee cartilage does not heal well due to lack of nerves, blood vessels and a lymphatic system. Hyaline cartilage in particular has a limited capacity for repair and lesions in this material without intervention, can form repair tissue lacking the biomechanical properties of normal cartilage.

A number of procedures are used to treat damaged articular cartilage. Currently, the most widely used procedure involves lavage, arthroscopic debridement and repair stimulation. Repair stimulation is conducted by drilling, abrasion arthroplasty or microfracture. The goal of this procedure is to penetrate into subchondral bone to induce bleeding and fibrin clot formation. This promotes initial repair. However, the resulting formed tissue is often fibrous in nature and lacks the durability of normal cartilage.

Osteochondral grafting has been used to repair chondral damage and to replace damaged articular cartilage and subchondral bone. In one such procedure, cartilage and bone tissue of a defect site are removed by routing to create a bore of a precise cylindrical geometry. Then a cylindrical cartilage and subchondral bone plug graft is harvested in a matching geometry. The harvest is typically from another body region of less strain. The plug graft can be harvested from a recipient source (autograft) or from another suitable human or other animal donor (allograft). The harvested plug graft is then implanted into the bore of the routed defect site. Healing of the graft bone to host bone results in fixation of the plug graft to surrounding host region.

Surface and other configuration characteristics of a plug graft are critical to achieving a successful implant. The surface of the transplanted graft must have the same contour as the excised osteochondral tissue. If the contour is not a correct match, a repaired articular surface is at risk for further damage. Also, the configuration of the plug graft must conform to a configuration of the recipient socket. Otherwise, a transplanted graft will be unstable and will move causing complications to the recipient area. Instability and movement result in poor integration of the plug graft with surrounding host tissue.

Instruments have been developed for harvest of plug grafts and for insertion for repair of a recipient patient's osteochondral tissue. These instruments can be unstable and difficult to control when the instruments are operated to harvest from a non uniform surface site such as a femoral trochlear groove. When activated in such areas, vibration can cause the instrument to "wander," meaning that the instrument strays along a site surface in varying cutting postures. Once the bit of the instrument wanders off-course, it is difficult to bring it back on center. The wander of the instrument makes it impossible to harvest a perpendicular and smooth walled plug graft from such sites.

There is a need for an instrument and method to harvest a perpendicular and smooth walled plug graft to avoid post implantation motion, graft surface mismatch and host tissue integration failure. There is a need for a kit to provide a surgeon with an instrument to harvest a normal configured plug graft for normal implant in a patient osteochondral tissue in need of repair.

BRIEF DESCRIPTION OF THE INVENTION

The invention relates to an instrument, method and kit to harvest a normal configured plug graft that avoids graft surface mismatch and tissue integration failure when implanted into a recipient tissue.

In a first embodiment, the invention is an instrument for harvesting an osteochondral plug graft in an implantable configuration, comprising: a support pod comprising an elongated tubular member distally terminating in at least three splayed legs; and a harvester encompassed within a longitudinal axis of the tubular member of the support pod.

In another embodiment, the invention is a method for harvesting an osteochondral plug graft, comprising: anchoring and stabilizing a harvesting instrument normal to an osteochondral plug graft donor site; and harvesting an osteochondral plug graft with the harvesting instrument.

In another embodiment, the invention is a kit for a surgical procedure, comprising: a plurality of differently configured drill bits; a plurality of pods differently configured to receive at least one of the plurality of drill bits within a bore of a pod; and at least one guide wire for insertion into a longitudinal axis of a drill bit.

BRIEF DESCRIPTION OF THE DRAWINGS

FIG. 2 is a schematic perspective view of an elongated tubular body;

FIG. 3 is a schematic perspective view of a guide wire;

FIG. 4 is a schematic perspective view of a drill bit;

DETAILED DESCRIPTION OF THE INVENTION

Figure 1:
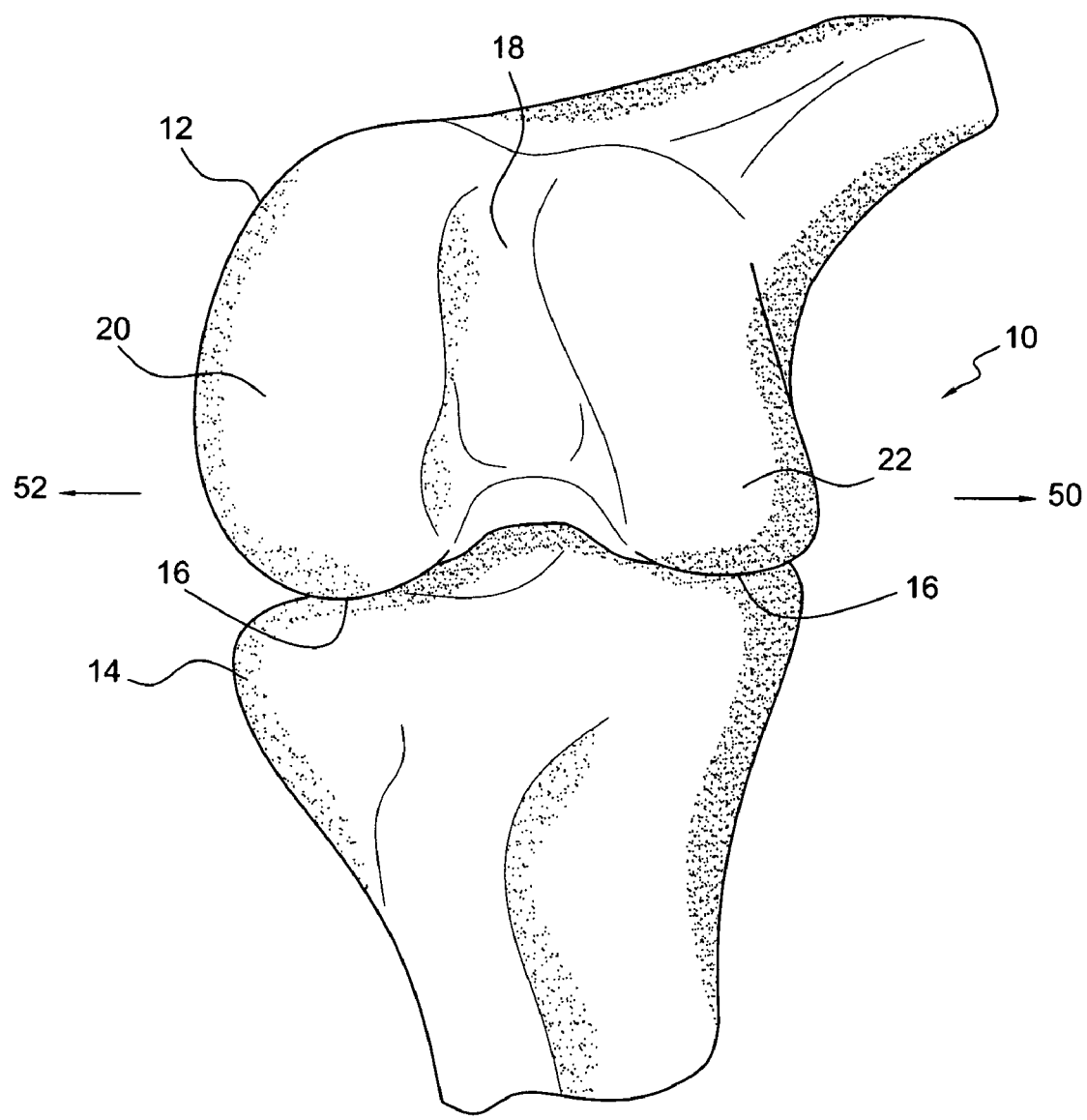
FIG. 1 is a schematic perspective view of a knee joint.

Perpendicular harvesting of a plug graft is important for proper treatment of a cartilage defect. If the plug graft is not smooth walled and in the form of a right angle prism to match a recipient socket corresponding form with a smooth wall and configured as a right angled prism, then surface contour of the cartilage layer on the harvested plug graft will not match the contour of the surrounding tissue. Additionally, the plug graft will not properly fit into the socket and will move to interfere with proper healing of the recipient osteochondral area. This eventually leads to failure of the bone plug as the plug graft, which will either subside or the cartilage layer on the plug will be damaged.

An embodiment of the invention uses a stabilizing pod, usually a tripod to aid in perpendicular harvesting. The tripod and a guide wire coordinate to stabilize a harvesting instrument to harvest a normal graft plug from an osteochondral donor site. Normal means at a right angle, substantially perpendicular to the surface of the osteochondral donor site. In the embodiment, first the guide wire is driven substantially perpendicular into the donor site. Once the guide wire is placed perpendicular all other parts of the harvesting instrument will drive over the guide wire to create a normal harvest. The tripod has a three point contact on the osteochondral donor site. The tripod legs are adjusted by the guide of the guide wire to define a plane tangential to the contour of the donor site. The feet of the tripod can be sharp so that the tripod does not move when driving a drill bit to ensure perpendicular harvesting.

Copending commonly assigned Shimko et al., U.S. application Ser. No. 11/340,884, filed Jan. 27, 2006, now U.S. Pat. No. 7,722,614 teaches an improved osteochondral implant fixation instrument and method that addresses an aspect of proper fit of a plug graft within a patient's osteochondral tissue. The disclosure of this Application is incorporated by reference into this specification in its entirety.

Shimko et al. teaches a surgical procedure comprising: inserting one end portion of a guide rod into the damaged area of a human, the remaining portion of the rod projecting out from the damaged area, advancing a hollow cutting blade having a rectangular cross section over the rod until the blade extends to the opening; exerting force on the cutting blade to form at least one planar surface in the damaged area that defines the opening; and removing the rod from the opening. An instrument for this process comprises a body member having a continuous bore for receiving a glide rod, and a hollow cutting blade for receiving the rod and having a rectangular cross section for cutting an opening having a rectangular cross section.

While Shimko et al. assures correct implantation fixation of a plug graft, an implant will fail if the harvested plug graft is improperly configured. There is a need for an instrument and method to harvest a properly configured plug graft to complement the normal implantation fixation of the Shimko et al. procedure.

Features of the invention will become apparent from the drawings and following detailed discussion, which by way of example without limitation describe preferred embodiments of the invention.

In the drawings, FIG. 1 is a schematic perspective view of a knee joint 10 (without patella), showing mating femur head 12 and tibia head 14. The knee joint 10 is oriented with lateral side 50 and medial side 52. Femur head 12 includes femoral articular surfaces 16, femoral trochlear groove 18, femoral medial condyle 20 and femoral lateral condyle 22. The FIG. 1 femoral trochlear groove 18 can represent a less strain area. A plug graft harvested from femoral trochlear groove 18 can be used to remedy an osteochondral defect, for example in an articular cartilage 16 of femur head 12.

Figure 5:
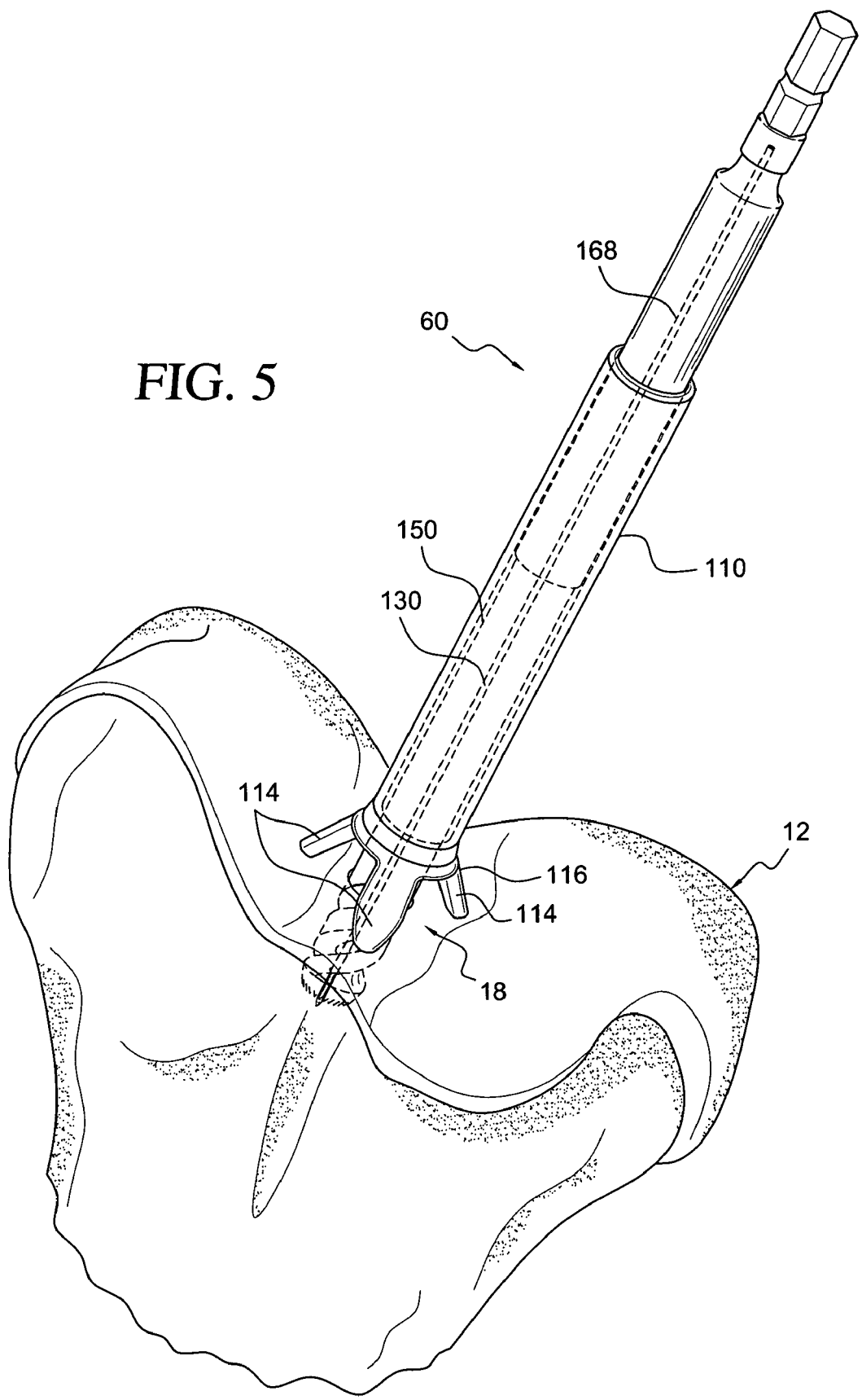
FIG. 5 is a schematic perspective view of an instrument harvesting an osteochondral plug graft from a femoral trochlear groove of the knee joint of FIG. 1.

According to an embodiment of the invention, an osteochondral plug graft is harvested from the trochlear groove 18 for implanting in place of a chondral area defect. FIGS. 2, 3 and 4 illustrate parts of an instrument 60 for harvesting the osteochondral plug graft according to an embodiment of the invention. FIG. 5 illustrates constructed instrument 60 positioned with femur head 12 to harvest the osteochondral plug graft from the femoral trochlear groove 16. In this embodiment, the instrument 60 includes the FIG. 2 pod 110 comprising an elongated tubular member 112, the FIG. 3 wire 130 and the FIG. 4 drill bit 150, arranged together as shown in FIG. 5.

In FIG. 2, the tubular member 112 includes a bore 120 that extends through a traverse length of elongated member 112. The pod 110 has a support structure 116 three legs 114 splayed outwardly at an angle from the longitudinal axis of elongated tubular member 112 to form a tripod configuration at distal end 118 of the member 112. The term "splayed" means oriented to diverge at equal angles away from the central longitudinal axis of the member 112. Further in FIG. 3 is shown bore 120 that traverses the member 112 from a proximal end 122 opening 124 to distal end 118 port 126. Port 126 is located within the splayed legs 114 configuration of the pod 110 as shown in FIG. 2 and FIG. 5.

In this application, a pod is a legged support structure. FIG. 2 shows a tripod configuration, a three legged support structure 116. However, the invention encompasses pod structures of any number of three or greater legs that can form a support structure 116 at the member distal end 118. The support structure 116 can be fabricated separately and attached to the elongated tubular member 112 in any usual manner.

FIG. 3 is an perspective view of a guide wire 130 and FIG. 4 is perspective view of a drill bit 150, which are included within the elongated tubular member 112 to form instrument 60 as shown in FIG. 5. Wire 130 is in the form of an elongated solid shaft 132 having a distal end 134 and proximal end 136 that align with the distal end 118 and the proximal end 122 of elongated tubular member 112 when included within the elongated tubular member 112 as shown in FIG. 5. The wire 130 has a threaded section 138 and brad 140 at its distal end 134. Brad 140 is a thin pointed piece that can be driven into an osteochondral material as a fastener as hereinafter described.

In the drawings, drill bit 150 represents a harvester that can be any osteochondral plug graft gatherer shaped to receive a plug graft from a donor site. For example, the harvester can be the drill bit 150 or a chisel as described hereinafter with respect to FIG. 6. In FIGS. 4 and 5, drill bit 150 includes an elongated body 152. The body 152 has distal end 154 and proximal end 156 that align with the distal end 118 and the proximal end 122 of elongated tubular member 112 when included within the elongated tubular member 112 again as shown in FIG. 5. The body 152 has a narrow bore passageway 168 partially extending through its length to accommodate insertion of the guide wire 130 with distal ends and proximal ends aligned as shown in FIG. 5. At proximal end 156, the elongated body 152 terminates in a solid shank 160 that accommodates attachment by means of a chuck of a drill for example.

The geometry of a cutting edge of a bit for harvesting plug grafts can be important in its performance because of the particular composition of an osteochondral area. Distal end 154 of drill bit 150 terminates in a curette-shaped trephine 158. The trephine 158 comprises saw like teeth 162 in a radial arrangement, used to cut out osteochondral plug grafts of cartilage and bone as hereinafter described. The trephine 158 is curette shaped meaning that the circumferential trephine 158 leading edge is slightly scoop shaped inwardly toward the longitudinal axis of body 152 to permit the removal of a routed plug graft from a harvest location. The trephine 158 end is a leading end to a flute cut out section 166 of the bit 150. The flute cut out section 166 serves to enhance the finish of a harvested plug graft surface.

In FIG. 5, guide wire 130 and drill bit 150 are shown nested within elongated body 112 to form instrument 60. Instrument 60 is assembled by inserting an end of the guide wire shaft 132 into the passageway 168 of the drill bit 150. The shaft 132 is inserted until seated within the full passageway 168 of the drill bit 150 with the threaded section 138 and brad 140 of the shaft extending from the passageway 168 bore. The combined guide wire 130 and drill bit 150 are inserted into the bore 120 of the pod 110 to form the nested instrument 60 illustrated in FIG. 5.

Additionally, FIG. 5 illustrates harvesting an osteochondral plug graft from a femoral trochlear groove 18 of a femur head 12. In FIG. 5, the instrument 60 is first set onto the trochlear groove 18 surface. The pod legs 114 are adjusted against the trochlear groove 18 surface until the instrument 60 is normal to the surface. Normal means that the instrument 60 is at a right angle substantially perpendicular to the surface of an osteochondral donor site such as trochlear groove 18. The normal oriented instrument 60 is substantially perpendicular to the direction of a plane tangent to the surface of an osteochondral donor site.

As shown in FIG. 5, the drill bit 150 is advanced over the guide wire 130 until the end of the trephine 158 saw teeth 162 rest on the trochlear 18 surface. The pod 110 is then placed over the drill bit 150 and guide wire 130. The threaded section 138 of the shaft 132 of the guide wire 130 is then driven or torqued into the trochlear groove 18 surface until the shaft 132 draws the legs 114 of the connected pod 110 to the trochlear groove 18 surface. The orientation of the instrument 60 is adjusted until the legs 114 are evenly tensioned and flush against the groove 18 surface. At this point, the pod 110 can be removed or left to stabilize the instrument 60 during the harvesting step of the process. The instrument 60 is both anchored and stabilized. The tripod support structure 116 acts to support and hold steady the pod 110 and consequently the drill bit 150 flush against the trochlear groove surface 18 and the imbedded guide wire anchors the tripod structure 116 in its supporting orientation to the surface 18.

The instrument can then be activated to perpendicularly harvest a plug graft from the trochlear groove surface 18. In one exemplary procedure, a mark is made on the body 152 of the drill bit 150 that extends a distance from the distal end 154 of the drill bit 150 corresponding to a desired depth of the plug graft to be harvested. The shank 160 of the drill bit 150 is engaged by a chuck of a hand or electric drill (not shown). The drill is activated at a relatively low RPM with little applied pressure until the radial teeth 162 of the trephine 158 penetrate the cartilage of the trochlear groove 18. The pressure on the bit 150 is then increased so that the teeth 162 of the trephine 158 start cutting the subchondral condyle. Cutting is continued until the marked portion of the body 152 extends even with the trochlear groove 18 surface.

Once cutting is completed, the curette shape of the trephine 158 will extract a plug from the cut area as the bit 150 and wire 130 are extracted from the trochlear groove 18 surface. The extracted plug graft comprises an articular cartilage layer and subchondral bone. The plug graft will have a right prism configuration according to the drill bit cut as directed by the tripod 116 and the guide wire 130. The right prism configuration will be suitable for implanting in a complementary right prism recipient socket of a patient. The recipient socked can be adapted using appropriately shaped reamers, curettes, press-fit expanders or dilators, or other general surgical instruments. For example in a process of repairing an osteochondral defect according to an embodiment of the invention, the defect is routed to form the recipient socket in a right prism cylindrical configuration to an exemplary depth of 4 to 6 mm.

While FIG. 5 shows harvest from a trochlear groove 18, the osteochondral plug graft of the invention can be harvested from any appropriate structure that includes hyaline cartilage and underlying subchondral bone. Suitable harvest locations include weight bearing joints of mammals, including humans. These harvest locations include articular cartilage and rib cartilage. A wide variety of human articular cartilages can be used including cartilage from articulating surfaces of the knee, hip and shoulder joints. As specific examples, an osteochondral plug graft can be taken from the femoral condyle, the articulating surface of the knee and the articulating surface of the shoulder.

Figure 6:
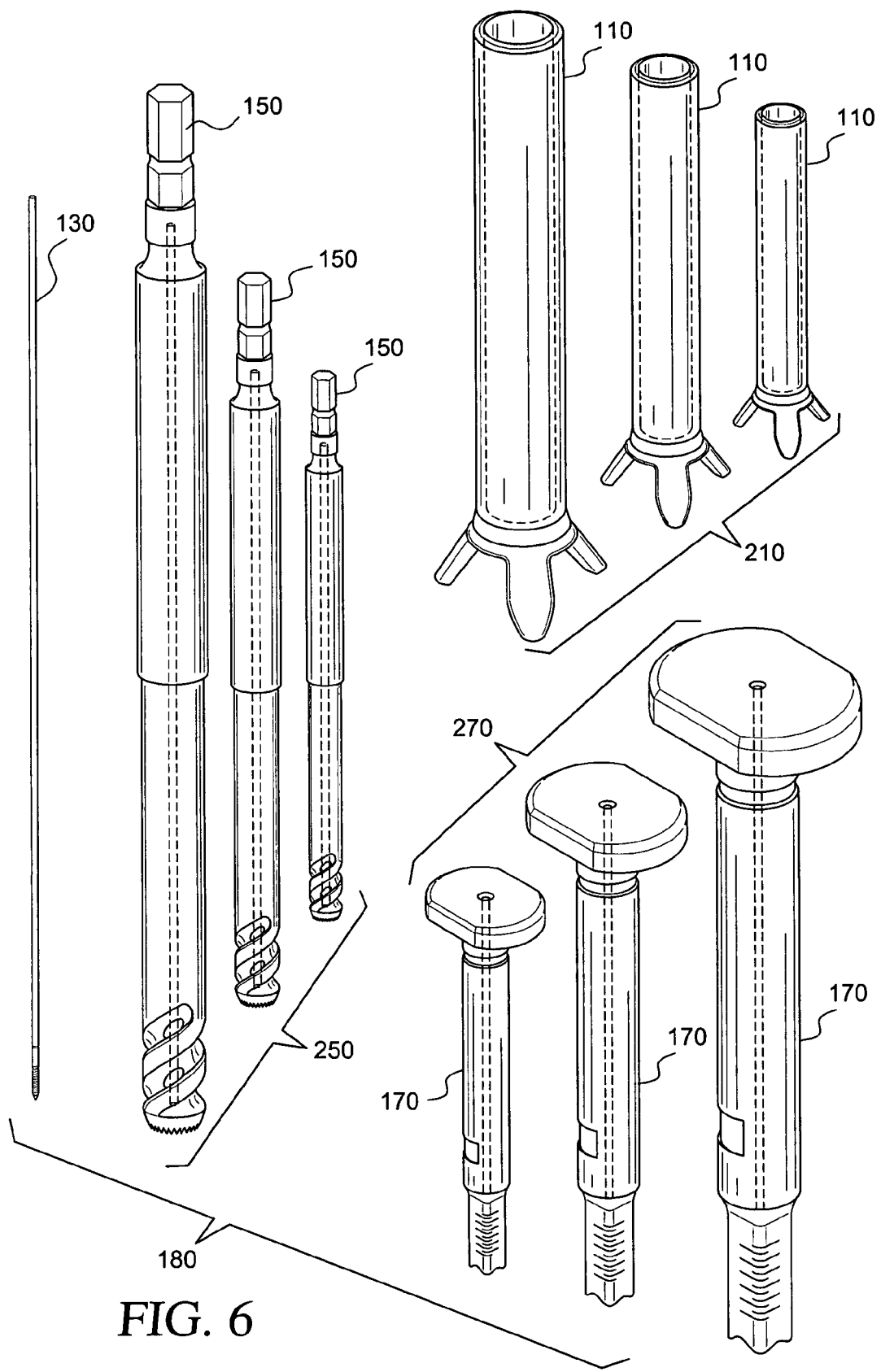
FIG. 6 is a schematic perspective view of a kit for carrying out a method of the invention.

FIG. 6 shows a kit 180 that can be used to practice an embodiment of the invention. In this embodiment, drill bits 150 are provided as an array 250 of bits and pods 110 are provided as an array 210 of pods included in kit 180. A drill bit 150 and a pod 110 can be selected from the respective arrays 250, 210 according to a desired configuration and size of a to be harvested plug graft. Further, the kit 180 includes guide wire 130, provided for insertion into a passageway 168 (shown in FIGS. 4 and 5) of a selected bit 150. Some of the pod array 210 pods 110 can have pointed leg ends for stabilization when used for plug harvesting and some pods 110 for implant can be smooth and curved to avoid damage to articular cartilage at a recipient site. The selected bit 150 with inserted wire 130 is then inserted into the bore 120 (FIGS. 3 and 6) for use in harvesting a plug graft in a desired configuration. Further, the kit 180 can include an array 270 of differently sized and/or configured chisels 170 for harvesting and also forming a recipient socket in a patient to accept implanting of the selected sized and/or configured plug grafts.

FIGS. 2 to 5 illustrate an embodiment of the invention including pod 110, wire 130 and a harvester, which is drill bit 150. In other embodiments of the invention, the harvester can be another device such as one of the chisels 170 shown in FIG. 5. In this embodiment, a selected chisel 170 can be fitted within a respective sized tripod, aligned onto a site and activated with an impact device such as an impact device such as a pneumatic rasp or broach impact device to either form a recipient socket or harvest a plug graft according to the invention. One such pneumatic device is the Bramstedt Surgical, Inc (1835 Energy Park Drive, St. Paul, Minn. 55108) Woodpecker® device.

The instrument of the invention can be used in at least two exemplary procedures with reference to FIG. 5. In a first method, first the drill bit 150 with inserted guide wire 130 is attached to an osteochondral harvesting site surface by driving guide wire 130 substantially normal to the site surface. Again, the femoral trochlear groove 18 is an exemplary harvesting site. Then, the pod 110 is placed over the bit 150 until legs 114 contact the harvesting site surface. The guide wire 130 is further inserted into the site 18 by driving or screwing the drill bit 150 into the surface of the site 18 to thereby draw the legs 114 of the pod 110 firmly to the site 18 surface in the perpendicular orientation dictated by the guide wire insertion.

In another method, the pod 110 is first placed at the site 18 so as to hold the drill bit 150 substantially normal to the site 18 surface. The drill bit 150 with inserted guide wire 130 is inserted through the pod bore 120 to emplace the wire 130 at the site 18 surface. Then the drill bit is driven or screwed to perpendicularly insert the guide wire 130 and at the same time to draw the legs 114 of the pod 110 to firmly fix the pod 110 to the site 18.

In either method, the final orientation of the drill bit is firmly maintained without wander or vibration in the normal position determined by the combined guidance and fixing of the pod and guide.

While preferred embodiments of the invention have been described, the present invention is capable of variation and modification and therefore should not be limited to the precise details of the drawing examples. For example, the invention has been described with reference to providing a plug graft normal to a harvesting site surface. However, in some cases a different configuration of plug graft may be required. In these instances, the instrument of the invention can be secured to harvest a plug graft of a different configuration, for example as a prism with sloping walls to fit a complementarily configured recipient socket. The invention includes changes and alterations that fall within the purview of the following claims.

What is claimed is:

1. An instrument for harvesting an osteochondral plug graft in an implantable configuration, comprising:
 a support pod comprising an elongated tubular member distally terminating in at least three splayed legs; and
 a harvester having a distal end and a proximal end, said harvester comprising an elongated hollow chamber extending form said proximal end to said distal end of said harvester and configured to nest a guide wire therein wherein at least a portion of said guide wire extends from said distal end of said harvester, said distal end of said harvester terminating in a curette shaped trephine with radial cutting teeth encompassed within a longitudinal axis of the tubular member of the support pod, said curette shaped trephine being a leading end to a flute cut out section of the harvester wherein said trephine defines a proximal end and distal end, said flute cut out section terminating at said proximal end of said trephine and said radial cutting teeth disposed at said distal end of said trephine such that said radial cutting teeth are disposed in a longitudinally spaced apart configuration from a terminate end of said flute cut out section.

2. The instrument of claim 1, wherein the harvester is a drill bit encompassed within a longitudinal axis of the tubular member of the support pod.

3. The instrument of claim 1, further comprising a guide wire encompassed within a longitudinal axis of the harvester and terminating at a threaded distal end for removably fixing a distal end of the instrument in a position oriented normal to an osteochondral surface for harvesting an osteochondral plug graft in an implantable normal configuration.

4. The instrument of claim 1, wherein the support pod comprises three legs oriented to diverge at equal angles away from a central longitudinal axis of the support pod.

5. The instrument of claim 1, wherein the harvester is a drill bit comprising an elongated body having a distal end and proximal end that align with the distal end and the proximal end of the elongated tubular member within a longitudinal passageway of the elongated tubular member.

6. The instrument of claim 1, wherein the harvester proximally terminates in a solid shank that accommodates attachment to a drill or impactor.

7. A kit for harvesting an osteochondral plug graft in an implantable configuration, comprising:
 a plurality of differently configured drill bits, at least one drill bit having a distal end and a proximal end, said at least one drill bit comprising an elongated hollow chamber extending form said proximal end to said distal end of said at least one drill bit and configured to nest a guide wire therein wherein at least a portion of said guide wire extends from said distal end of said at least one drill bit, said distal end of said at least one drill bit distally terminating in a curette shaped trephine with radial cutting teeth, said curette shaped trephine being a leading end to a flute cut out section of the bit wherein said trephine defines a proximal end and distal end, said flute cut out section terminating at said proximal end of said trephine and said radial cutting teeth disposed at said distal end of said trephine such that said radial cutting teeth are disposed in a longitudinally spaced apart configuration from a terminate end of said flute cut out section;
 a plurality of pods differently configured to receive at least one of the plurality of drill bits within a bore of a pod; and
 at least one guide wire for insertion into a longitudinal axis of a drill bit.

8. The kit of claim 7, further comprising a plurality of chisels to form a recipient socket in an osteochondral area in need of repair or to harvest a plug graft to implant into a recipient socket.

9. The kit of claim 7, wherein at least one support pod comprises three legs oriented to diverge at equal angles away from a central longitudinal axis of the support pod.

10. The kit of claim 7, wherein at least one wire terminates in a brad at its threaded distal end that is a thin pointed piece that can be driven or screwed into an osteochondral material as a fastener.

11. The kit of claim 7, wherein at least one pod comprises an elongated tubular member having a distal end and proximal end and wherein at least one guide wire comprises a solid shaft that aligns with the distal end and the proximal end of the elongated tubular member within a longitudinal passageway of the elongated tubular member when included within the elongated tubular member.

12. The instrument of claim 1, wherein the guide wire terminates in a brad at its threaded distal end that is a thin pointed piece that can be driven or screwed into an osteochondral material as a fastener.

13. The instrument of claim 1, wherein the pod comprises an elongated tubular member and the guide wire comprises an elongated solid shaft having a distal end and proximal end that align with a distal end and a proximal end of the elongated tubular member when included within the elongated tubular member.

* * * * *